United States Patent [19]
Lattner et al.

[11] Patent Number: 6,023,005
[45] Date of Patent: *Feb. 8, 2000

[54] PROCESS FOR CONVERTING OXYGENATES TO OLEFINS USING MOLECULAR SIEVE CATALYSTS COMPRISING DESIRABLE CARBONACEOUS DEPOSITS

[75] Inventors: James Richardson Lattner, Seabrook; Hsiang-ning Sun, Houston; Stephen Neil Vaughn, Kingwood; Keith H. Kuechler, Friendswood, all of Tex.; David C. Skouby, Flanders, N.J.

[73] Assignee: Exxon Chemicals Patents Inc., Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/887,766

[22] Filed: Jul. 3, 1997

[51] Int. Cl.[7] ................................ C07C 1/00; B01J 20/34
[52] U.S. Cl. .......................... 585/639; 585/638; 585/640; 502/38
[58] Field of Search ............................... 502/38; 585/638, 585/639, 640

[56] References Cited

U.S. PATENT DOCUMENTS

| | | | |
|---|---|---|---|
| 4,338,475 | 7/1982 | Pennington et al. | 585/408 |
| 4,431,856 | 2/1984 | Daviduk et al. | 585/469 |
| 4,440,871 | 4/1984 | Lok et al. | 502/214 |
| 4,499,327 | 2/1985 | Kaiser | 585/640 |
| 4,677,242 | 6/1987 | Kaiser | 585/638 |
| 4,677,243 | 6/1987 | Kaiser | 585/638 |
| 4,752,651 | 6/1988 | Kaiser | 585/640 |
| 4,861,938 | 8/1989 | Lewis et al. | 585/640 |
| 4,873,390 | 10/1989 | Lewis et al. | 585/638 |
| 5,095,163 | 3/1992 | Barger | 585/640 |
| 5,157,181 | 10/1992 | Stine et al. | 585/329 |
| 5,191,141 | 3/1993 | Barger et al. | 585/640 |
| 5,714,662 | 2/1998 | Vora et al. | 585/640 |
| 5,714,663 | 2/1998 | Serrand et al. | 585/648 |

OTHER PUBLICATIONS

Methanol Conversion to Light Olefins (Clarence D. Chang) (1984).
Production of Chemicals from Methanol (Warren W. Kaeding & Stephen A. Butter) (1980).
Converting Natural Gas to Ethylene and Propylene by the UOP/Hydro MTO Process (Barger et al.) (12th International Zeolite Conference, 1999 Materials Research Society).
PCT/US 98/13404 International Search Report.
Zeolites, vol. 17, pp. 212–222 (1996).
Zeolites, vol. 17, pp. 512–222 (1996).
W. M. Meier and D. H. Olsen, Atlas of Zeolite Strutural Types (Butterworth Heineman–3rd ed. 1997).
Zeolites, vol. 17, pp. 512–522 (1996).

*Primary Examiner*—Marian C Knode
*Assistant Examiner*—In Suk Bullock
*Attorney, Agent, or Firm*—Linda Russell; Bradley Keller

[57] ABSTRACT

The present invention relates to methods for selectively converting oxygenates to light olefins, preferably ethylene and propylene, in which desirable carbonaceous deposits are maintained on a total reaction volume of catalyst by totally regenerating only a portion of the total reaction volume of catalyst and mixing the regenerated portion with the unregenerated total reaction volume of catalyst.

42 Claims, 1 Drawing Sheet

PROCESS FOR CONVERTING OXYGENATES TO OLEFINS USING MOLECULAR SIEVE CATALYSTS COMPRISING DESIRABLE CARBONACEOUS DEPOSITS

FIELD OF THE INVENTION

The present invention relates to methods for selectively converting oxygenates to light olefins, preferably ethylene and propylene, in which desired carbonaceous deposits are maintained on a total reaction volume of catalyst by totally regenerating only a portion of the total reaction volume of catalyst and mixing the regenerated portion with the unregenerated total reaction volume of catalyst.

BACKGROUND OF THE INVENTION

Light olefins (defined as "ethylene, propylene, and butylene") serve as feeds for the production of numerous chemicals. Light olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the selectivity of molecular sieve catalysts to ethylene and/or propylene. The selectivity of certain molecular sieve catalysts to ethylene and propylene is known to increase if the level of coke on the total reaction volume of molecular sieve catalyst is maintained in the range of from about 2 wt % to about 30 wt %. Some have suggested maintaining this desired level of coke by removing all or a portion of the total reaction volume of catalyst, partially regenerating the catalyst so removed, and returning the partially regenerated catalyst to the reactor. However, partial regeneration may not result in maximum selectivity of the catalyst to light olefins.

Methods are needed which will maintain a desired level of coking on molecular sieve catalysts during the conversion of oxygenates to olefins while maintaining maximum activity of the catalyst.

SUMMARY OF THE INVENTION

The present invention provides a method for treating a molecular sieve catalyst comprising: contacting a feed comprising oxygenates with a total reaction volume of a molecular sieve catalyst under conditions effective to produce a stream comprising $C_2$–$C_3$ olefins, wherein said total reaction volume comprises desirable carbonaceous deposits which render said catalyst more selective to $C_2$–$C_3$ olefins than in the absence of said desirable carbonaceous deposits; and wherein, upon accumulation of undesirable carbonaceous deposits effective to interfere with catalyst activity, said desirable carbonaceous deposits are maintained on said molecular sieve catalyst by a process comprising: separating said total reaction volume of molecular sieve catalyst into a portion and a remainder; treating said portion with a regeneration medium under conditions effective to remove said undesirable carbonaceous deposits, forming a regenerated portion comprising in the range of from about 0 wt % to a regenerated amount of carbonaceous deposits; and, mixing said regenerated portion with said remainder, wherein said regenerated amount of carbonaceous deposits comprises an amount sufficient, upon said mixing, to produce a regenerated total reaction volume comprising said desirable carbonaceous deposits.

DETAILED DESCRIPTION OF THE INVENTION

Figure 1:
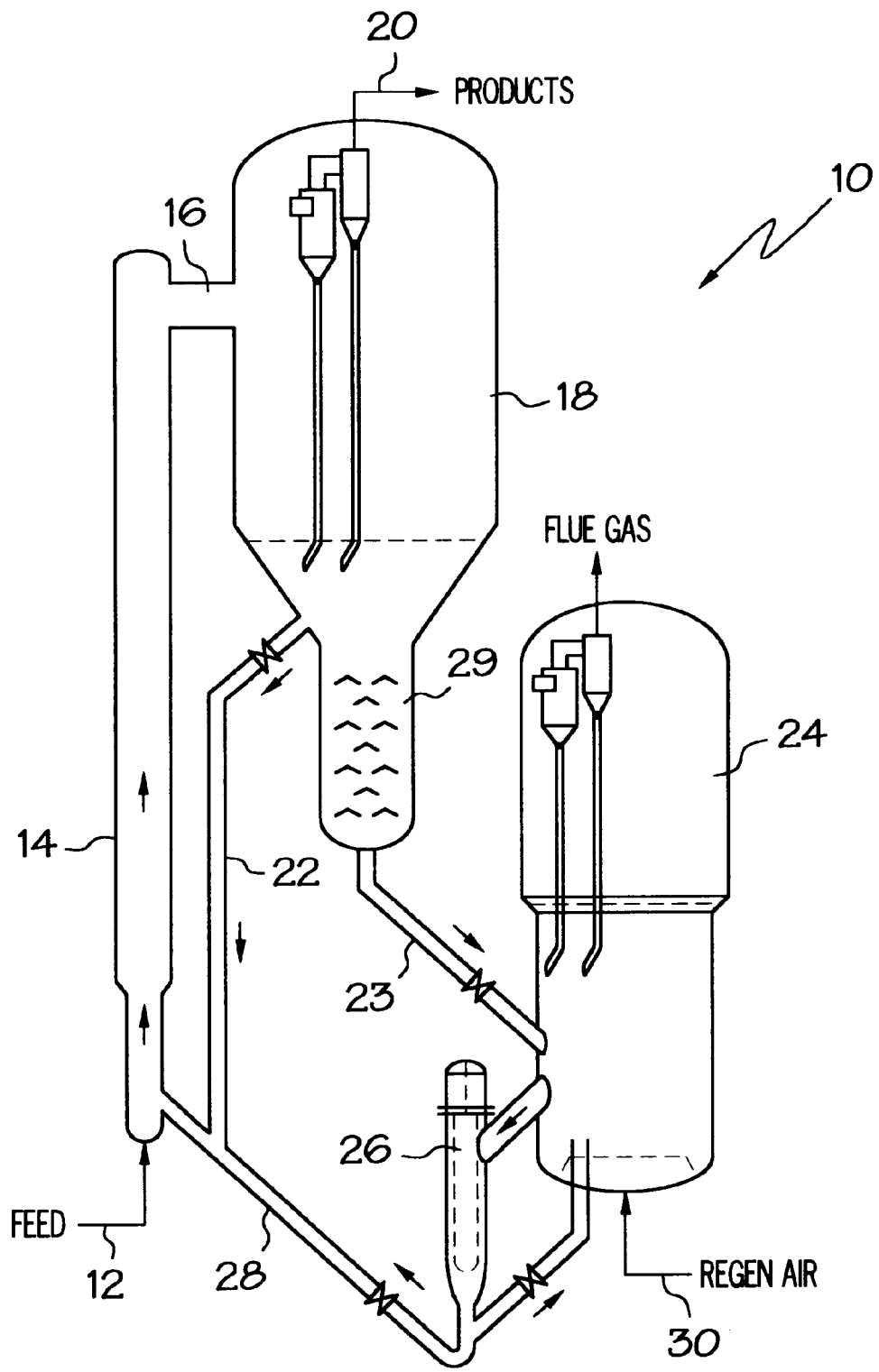
FIG. 1 is a diagram of a preferred embodiment of a high velocity fluid bed reactor with catalyst recirculation for use in the present invention.

The conversion of oxygenates to light olefins is catalyzed by various molecular sieve catalysts. Due to the high temperatures required during the conversion process, carbonaceous deposits known as "coke" unavoidably form on the surface of the molecular sieve catalyst. In order to avoid a significant reduction in catalyst activity, the catalyst must be regenerated by burning off coke deposits.

One goal during the conversion of oxygenates to olefins is to maximize the production of light olefins, preferably ethylene and propylene, and to minimize the product of methane, ethane, propane, and $C_5$+materials. The present invention uses the coke that unavoidably deposits on the catalyst to achieve this goal by allowing "desirable carbonaceous deposits" to accumulate on the molecular sieve catalyst while removing undesirable carbonaceous deposits.

One method that has been suggested to maintain desirable carbonaceous deposits on the catalyst is to only partially regenerate some or all of the total reaction volume of molecular sieve catalyst. Without limiting the present invention to a particular theory, it is believed that only partially regenerating a portion or only partially regenerating all of a total reaction volume of coked molecular sieve catalyst has a serious drawback. Coke that is produced during the conversion of oxygenates to olefins is known to deposit both on the surface and in the "micropores" of molecular sieve catalysts. The reactions that selectively convert oxygenates to ethylene and propylene occur in the micropores of the molecular sieve catalyst. It is relatively difficult for a regeneration medium (usually oxygen) to access the micropores. Because of this, coke that builds up in the micropores is more difficult to remove during the regeneration process. Partial regeneration most likely does not remove the coke from the micropores of the catalyst, which result in an adverse impact on the selectivity of the catalyst to ethylene and propylene.

The present invention maintains "desirable carbonaceous deposits" on the catalyst by removing only a portion of the total reaction volume of coked molecular sieve catalyst and totally regenerating only that portion of catalyst. Total regeneration is believed to remove coke from both the micropores and from the less selective surface areas of the regenerated portion of the catalyst. When the regenerated portion of catalyst is mixed with the unregenerated remainder of the catalyst, the result is the maintenance of desirable carbonaceous deposits blocking less selective surface areas in the unregenerated portion of the catalyst, and an increase in the sites available to selectively convert oxygenates to light olefins (micropore surface area) in the regenerated portion of the catalyst.

As used herein, the term "desirable carbonaceous deposits" is defined to comprise an amount of at least about 2 wt % carbonaceous deposits, preferably in the range of from about 2 wt % to about 30 wt % carbonaceous deposits, based on the weight of the total reaction volume of coked catalyst. "Desirable carbonaceous deposits"—even if they comprise over 30 wt % of the total reaction volume of molecular sieve catalyst—are carbonaceous deposits which primarily block portions of the surface of the catalyst that are not selective to the production of $C_2$–$C_3$ olefins.

Substantially any small or medium pore molecular sieve catalysts and equivalents thereof may be used in to the present invention. "Small pore molecular sieve" catalysts are defined as catalysts with pores having a diameter of less than about 5.0 Angstroms. Medium pore molecular sieve catalysts are defined as catalysts with pores having a diameter of in the range of from about 5 and 10 Angstroms. "Equivalents thereof" is defined to refer to catalysts having a pore size that performs substantially the same function in substantially the same way to achieve substantially the same result as catalysts having the foregoing diameter or pore size.

One group of suitable molecular sieve catalysts is the zeolite group. Several types of zeolites exist, each of which exhibit different properties and different utilities. Structural types of small pore zeolites that are suitable for use in the present invention with varying levels of effectiveness include, but are not necessarily limited to AEI AFT, APC, ATN, ATT, ATV, AWW, BIK CAS, CHA, CHI, DAC, DDR, EDI, ERI, GOO, KFI, LEV, LOV, LTA, MON, PAU, PHI, RHO, ROG, and THO and substituted examples of these structural types, as described in W. M. Meier and D. H. Olsen, *Atlas of Zeolite Structural Types* (Butterworth Heineman—3rd ed. 1997), incorporated herein by reference. Preferred zeolite catalysts include, but are not necessarily limited to, ZSM-5, ZSM-34, erionite, and chabazite.

Silicoaluminophosphates ("SAPO's") are another group of molecular sieve catalysts that are useful in the invention. SAPO's have a three-dimensional microporous crystal framework of $PO_2^+$, $AlO_2^-$, and $SiO_2$ tetrahedral units. Suitable SAPO's for use in the invention include, but are not necessarily limited to SAPO-34, SAPO-17, and SAPO-18. A preferred SAPO is SAPO-34, which may be synthesized according to U.S. Pat. No. 4,440,871, incorporated herein by reference, and *Zeolites*, Vol. 17, pp. 512–522 (1996), incorporated herein by reference.

SAPO's with added substituents also may be useful in the present invention. These substituted SAPO's form a class of molecular sieves known as "MeAPSO's." Substituents may include, but are not necessarily limited to nickel, cobalt, strontium, barium, and calcium.

Structural types of medium pore molecular sieves useful in the present invention include, but are not necessarily limited to, MFI, MEL, MTW, EUO, MTT, HEU, FER, AFO, AEL, TON, and substituted examples of these structural types, as described in the *Atlas of Zeolite Types*, previously incorporated herein by reference.

The process for converting oxygenates to olefins employs an organic starting material (feedstock) preferably comprising "oxygenates." As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof The aliphatic moiety preferably should contain in the range of from about 1–10 carbon atoms and more preferably in the range of from about 1–4 carbon atoms. Representative oxygenates include, but are not necessarily limited to, lower straight chain or branched aliphatic alcohols, their unsaturated counterparts, and their nitrogen, halogen and sulfur analogues. Examples of suitable compounds include, but are not necessarily limited to: methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. As used herein, the term "oxygenate" designates only the organic material used as the feed. The total charge of feed to the reaction zone may contain additional compounds, such as diluents.

Preferably, the oxygenate feedstock should be contacted in the vapor phase in a reaction zone with the defined molecular sieve catalyst at effective process conditions so as to produce the desired olefins, i.e., an effective temperature, pressure, WHSV (Weight Hourly Space Velocity) and, optionally, an effective amount of diluent. Alternately, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

The temperature employed in the conversion process may vary over a wide range depending, at least in part, on the selected catalyst. Although not limited to a particular temperature, best results will be obtained if the process is conducted at temperatures in the range of from about 200° C. to about 700° C., preferably in the range of from about 250° C. to about 600° C., and most preferably in the range of from about 300° C. to about 500° C. Lower temperatures generally result in lower rates of reaction, and the formation of the desired light olefin products may become markedly slow. However, at higher temperatures, the process may not form an optimum amount of light olefin products, and the coking rate may become too high.

Light olefin products will form—although not necessarily in optimum amounts—at a wide range of pressures, including but not limited to autogeneous pressures and pressures in the range of from about 0.1 kPa to about 100 MPa. A preferred pressure is in the range of from about 6.9 kPa to about 34 MPA, most preferably in the range of from about 48 kPa to about 0.34 MPA. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor), and the selected process design characteristics.

A wide range of weight hourly space velocities (WHSV) for the feedstock will function in the present invention. WHSV is defined as weight feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, preferably in the range of from about 0.5 $hr^{-1}$ to about 300 $hr^{-1}$, and most preferably in the range of from about 0.1 $hr^{-1}$ to about 200 $hr^{-1}$. One or more diluents may be fed to the reaction zone with the oxygenates, such that the total feed mixture comprises diluent in a range of from about 1 mol % to about 99 mol %. Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Preferred diluents are water and nitrogen.

A preferred embodiment of a reactor system for the present invention is a circulating fluid bed reactor with continuous regeneration, similar to a modem fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

It is important for the reactor to be designed such that a relatively high average level of coke is maintained in the reactor—an amount greater than about 1.5 wt %, preferably in the range of from about 2 wt % to about 30 wt %, most preferably in the range of from about 2 wt % to about 20 wt %. If the reactor is a high velocity fluidized bed reactor (sometimes referred to as a riser reactor), then a portion of the catalyst exiting the top of the reactor must be returned to the reactor inlet. This is different from a typical Fluid Catalytic Cracker (FCC) riser reactor, where all or most of the catalyst exiting the top of the reactor is sent to the regenerator. The return of coked catalyst directly to the reactor, without regenerating the coked catalyst, allows the average coke level in the reactor to build up to a preferred level. By adjusting the ratio of the flow of the coked catalyst between the regenerator and the reactor, a preferred level of coking, or "desirable carbonaceous deposits," can be maintained.

If the fluidized bed reactor is designed with low gas velocities, below about 2 m/sec, then cyclones may be used to return catalyst fines to the fluidized bed reaction zone. Such reactors generally have high recirculation rates of solids within the fluidized bed, which allows the coke level on the catalyst to build to a preferred level. Desirable carbonaceous deposits are maintained by withdrawing catalyst from the bed and regenerating the catalyst in the manner described above, and then returning at least a portion of this regenerated catalyst to the reactor.

A preferred embodiment of a riser reactor configuration for use in the present invention is depicted generally as 10 in FIG. 1. A methanol feed 12 is at least partially vaporized in a preheater (not shown). The methanol feed is mixed with regenerated catalyst 28 and coked catalyst 22 at the bottom of the riser reactor 14. An inert gas and/or steam may be used to dilute the methanol, lift the catalyst streams 22 and 28, and keep pressure instrument lines clear of catalyst. This inert gas and/or steam mixes with the methanol and catalyst in the reactor 14. The reaction is exothermic, and the preferred reaction temperature, in the range of from about 300° C. to about 500° C., is maintained by removing heat. Heat can be removed by any suitable means, including but not necessarily limited to cooling the reactor with a catalyst cooler (not shown), feeding some of the methanol as a liquid, cooling the catalyst feed to the reactor, or any combination of these methods.

The reactor effluent 16, containing products, coked catalyst, diluents, and unconverted feed, should flow to a disengaging zone 18. In the disengaging zone 18, coked catalyst is separated from the gaseous materials by means of gravity and/or cyclone separators. A portion of the coked catalyst 22 is returned to the reactor inlet. The portion of coked catalyst 22 to be regenerated is first sent to a stripping zone 29, where steam or other inert gas is used to recover adsorbed hydrocarbons from the catalyst. Stripped spent coked catalyst 23 should flow to the regenerator 24. The portion of the catalyst sent to the regenerator 24 should be contacted with a regeneration medium, preferably a gas comprising oxygen 30, at temperatures, pressures, and residence times that are capable of burning coke off of the catalyst and down to a level of less than about 0.5 wt %. The preferred temperature in the regenerator is in the range of from about 550° C. to about 700° C., the preferred oxygen concentration in the gas leaving the regenerator is in the range of from about 0.1 vol % to about 5 vol %, and the preferred residence time is in the range of from about 1 to about 100 minutes.

The burning off of coke is exothermic. The temperature may be maintained at a suitable level by any acceptable method, including but not limited to feeding cooler gas, cooling the catalyst in the regenerator with a cat cooler 26, or a combination of these methods.

The regenerated catalyst 28 is sent to the reactor 14, where it mixes with the recirculated coked catalyst 22 and the methanol feed 12. The regenerated catalyst 28 may be lifted to the reactor 14 by means of an inert gas, steam, or methanol vapor (not shown). The process should repeat itself in a continuous or semi-continuous manner. The hot reactor product gases 20 should be cooled, the water byproduct condensed and collected, and the desired olefin product gases recovered for further processing.

In order to determine the level of coke in the reactor and in the regenerator, small samples of catalyst periodically may be withdrawn from various points in the recirculating system for measurement of carbon content. The reaction parameters may be adjusted accordingly.

The following examples illustrate, but do not limit, the present invention.

EXAMPLE 1

A continuous circulating fluid bed reactor was charged with 3200 g of catalyst, which was spray dried from a mixture of SAPO-34 powder (obtained from UOP, Des Plaines, Ill.) with alumina and clay binders having an average particle size of 90–100 microns. In three different tests, neat methanol was charged at a rate of 900 grams/hour and vaporized in a preheater. The vaporized feed was mixed with 20,000 to 25,000 grams/hour of catalyst, and fed to a reactor with a 1.02 cm (0.4 inch) inner diameter and a length of 6.71 meters (22 feet). About 268.21 liters/hr (7 scf/hr) of nitrogen was used to lift the catalyst and keep pressure instruments clear of catalyst fines. The nitrogen mixed with the methanol and catalyst in the reactor. The temperature in the reactor was maintained at 450° C. by means of electric heaters. The effluent from the reactor flowed to a stripper, where the catalyst was removed from the product gas. The catalyst was contacted with nitrogen in the bottom of the stripper to recover volatile hydrocarbons from the catalyst. The stripped catalyst was sent to a regenerator, where the catalyst was contacted with a mixture of nitrogen and air. The temperature in the regenerator was maintained at 620° C. with electric heaters, and the air rate could be varied to adjust the coke level on the regenerated catalyst. The catalyst from the regenerator was returned to the reactor, where it mixed with the methanol feed. The process repeated itself in a continuous manner. The hot reactor product gases were cooled, and the water byproduct condensed and collected. The hydrocarbon gases were separated from the water and analyzed by GC. The flue gas from the regenerator was analyzed for oxygen, carbon monoxide, and carbon dioxide, and the rate was measured in a dry test meter. Small samples of catalyst were periodically withdrawn from both the stripper and the regenerator for measurement of carbon content. Based on these measurements, the yield of products, including coke, were calculated.

In test 1, the air rate was set so that nearly all of the carbon on the catalyst was removed during each pass through the regenerator. The carbon content on the catalyst leaving the reactor was 0.5 wt %, and the regenerator removed all but 0.2 wt % of this carbon. The selectivity to ethylene was 10.8 wt % and the selectivity to heavies and coke was 34.9 wt % and 14.3 wt %, respectively.

In test 2, the air rate to the regenerator was reduced so that all of the catalyst was only partially regenerated at each pass. The carbon on the circulating catalyst increased, eventually reaching a steady state such that carbon was removed at the same rate that it was deposited. At this point, the carbon on catalyst to the regenerator was 5.5%, and the carbon content of the catalyst leaving the regenerator was 4.9%. The selectivity to ethylene improved to 26.7%, and the selectivity to undesirable heavies decreased to 17.9%. The coke yield remained relatively unchanged at 13.6%. The methanol conversion was 91.3%, showing a decline in the catalyst activity due to the coke on the catalyst.

In test 3, the methanol feed was stopped and the circulating catalyst was allowed to be fully regenerated (down to 0.15 wt % carbon). Then the air to the regenerator was stopped, the methanol feed was reintroduced, and coke was allowed to build up on the catalyst without regeneration for about 5 hours. The carbon content on the circulating catalyst after 5 hours was 5.8%. At this point, the selectivity to ethylene had improved to 35.0%, the heavies selectivity was further reduced to 13.4%, and the selectivity to coke was reduced to 4.1%. The coke yield was calculated from measurements of the carbon accumulation on the catalyst over the previous hour on oil. The conversion at this point was 89.9%, showing that the catalyst had roughly the same activity as the catalyst in test 2.

Following test 3, the reactor was returned to the same operating conditions as in test 1, and then test 2. The methanol conversions and product yields essentially were the same as the original yields in test 1 and 2 after a total of 150 hours on oil, showing that the results were not simply the effect of catalyst aging.

Column 4 represents a calculated product selectivity for a commercial reactor using the present invention, based on the data from Tests 1 and 3. Column 4 assumes that 10% of the methanol is converted over freshly regenerated catalyst (selectivities according to test 1), and the remaining 90% of the methanol is converted over coked catalyst (selectivities according to test 3). The calculated selectivities are slightly worse than the results of test 3, but still are significantly better than would be obtained if the catalyst was only partially regenerated, as in test 2:

| Test No. | 1 | 2 | 3 | 4 (calculated) |
|---|---|---|---|---|
| Regeneration Mode | Complete regeneration of all of the catalyst | Partial regeneration of all of the catalyst | None | Complete regeneration of a portion of catalyst |
| Carbon on catalyst leaving reactor | 0.5% | 5.5% | 5.8% | 5.3% |
| Carbon on catalyst leaving regenerator | 0.2% | 4.9% | 5.8% | 0.2% |
| Methanol conversion | 97.8% | 91.3% | 89.9% | 90.7% |
| Selectivities*: | | | | |
| Hydrogen | 0.1 | 0.2 | 0.1 | 0.1 |
| Methane | 3.1 | 2.1 | 4.0 | 3.9 |
| Ethane | 0.4 | 0.5 | 0.9 | 0.9 |
| Ethylene | 10.8 | 26.7 | 35.0 | 32.6 |
| Propane | 5.1 | 0.7 | 0.2 | 0.7 |
| Propylene | 16.0 | 24.4 | 27.5 | 26.4 |
| Butenes | 14.9 | 14.0 | 14.1 | 14.2 |
| Heavies | 34.9 | 17.9 | 13.4 | 15.6 |
| $CO_2$ | 0.3 | 0.1 | 0.6 | 0.6 |
| Coke | 14.3 | 13.6 | 4.1 | 5.1 |

*"Selectivities" are on a water-free basis

The foregoing results demonstrated that coked catalysts (~5% on catalyst) achieved higher selectivities to ethylene and propylene than catalysts having coke levels less than 1%. The results also showed that totally regenerated catalyst which was allowed to accumulate coke achieved higher selectivities than catalyst that was partially regenerated to reduce the same coke to the same level. These results are consistent with the theory that partial regeneration of coke selectively removes coke that is blocking undesirable surface reactions that form propane and $C_5$+materials. The reactions that selectively make ethylene and propylene occur in the small pores, and the coke that accumulates in these pores is more difficult to remove than the outer surface (macropore) coke. When a "clean" catalyst is allowed to coke, the coke deposits faster on the macropore surfaces than in the micropores, slowing the non-selective surface reactions, thus accounting for the improved selectivities for "coked" versus "clean" catalyst. As more and more coke accumulates, however, the catalyst eventually becomes inactive. The activity is restored by regeneration with air, but it is important that the catalyst be fully burned to remove as much carbon as possible, and then allowed to coke up again in the reactor. Partial regeneration of the catalyst, as taught in U.S. Pat. No. 4,873,390 to Lewis, was not nearly as effective at maintaining ethylene and propylene selectivity in the reactor.

Based on the foregoing, it was concluded that better selectivity to light olefins can be achieved in an oxygenate to olefin conversion if desirable coke is maintained on a total reaction volume of molecular sieve catalyst by totally regenerating only a portion of the catalyst and returning at least a part of the regenerated portion to the total reaction volume.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process for converting an oxygenate feedstock into an olefin product stream comprising:
   (a) contacting the oxygenate feedstock with a molecular sieve catalyst under conditions effective to convert the feedstock into an olefin product stream comprising $C_2$–$C_3$ olefins and to form carbonaceous deposits on the catalyst;
   (b) separating the catalyst having the carbonaceous deposits into a portion and a remainder;
   (c) contacting the portion with a regeneration medium under conditions effective to obtain a regenerated catalyst portion having less than 1.0 wt % carbonaceous deposits;
   (d) mixing the regenerated catalyst portion with the remainder wherein the mix of the regenerated catalyst portion and the remainder comprises 2–30 wt % carbonaceous deposits; and
   (e) repeating steps (a)–(d).

2. The process of claim 1, wherein the regenerated catalyst portion comprises 0.5 wt % or less carbonaceous deposits.

3. The process of claim 1, wherein the mix of the regenerated catalyst portion and the remainder comprises 2–20 wt % carbonaceous deposits.

4. The process of claim 1, wherein the oxygenate feedstock is contacted with the molecular sieve catalyst in a riser reactor.

5. The process of claim 4, wherein the remainder is recycled directly to the riser reactor, without regenerating the remainder.

6. The process of claim 5, wherein the portion is sent to a regenerator and contacted with the regeneration medium in the regenerator to obtain a regenerated catalyst portion, and the regenerated catalyst portion is mixed with the remainder, and returned to the riser reactor.

7. The process of claim 1, wherein the molecular sieve catalyst has a pore diameter of less than 5.0 Angstroms.

8. The process of claim 7, wherein the molecular sieve catalyst is at least one catalyst selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted groups thereof.

9. The process of claim 7, wherein the molecular sieve catalyst is at least one catalyst selected from the group consisting of ZSM-5, ZSM-4, erionite, and chabazite.

10. The process of claim 7, wherein the molecular sieve catalyst is at least one catalyst selected from the group consisting of SAPO-34, SAPO-17, and SAPO-18.

11. The process of claim 7, wherein the molecular sieve catalyst is a MeAPSO.

12. The process of claim 1, wherein the molecular sieve catalyst has a pore diameter of 5–10 Angstroms.

13. The process of claim 12, wherein the molecular sieve catalyst is at least one catalyst selected from the group consisting of MFI, MEL, MTW, EUO, MTT, HEU, FER, AFO, AEL, TON, and substituted groups thereof.

14. The process of claim 1, wherein the oxygenate feedstock comprises at least one compound is selected from the group consisting of methanol, ethanol, n-propanol, isopropanol, C4–C10 alcohols, methyl ether, dimethyl ether, diethyl ether di-isopropyl ether, methyl mercaptan, methyl sulfide, methyl amine, ethyl mercaptan, di-ethyl sulfide, di-ethyl amine, ethyl chloride, formaldehyde, di-methyl carbonate, di-methyl ketone, acetic acid, n-alkyl amines, n-alkyl halides, and n-alkyl sulfides, wherein the n-alkyl groups comprise from 3–10 carbon atoms.

15. The process of claim 1, wherein the oxygenate feedstock is contacted with the molecular sieve catalyst at a temperature in the range of 200–700° C.

16. The process of claim 15, wherein the oxygenate feedstock is contacted with the molecular sieve catalyst at a temperature in the range of 250–600° C.

17. The process of claim 16, wherein the oxygenate feedstock is contacted with the molecular sieve catalyst at a temperature in the range of 300–500° C.

18. The process of claim 15, wherein the oxygenate feedstock is contacted with the molecular sieve catalyst at a pressure in the range of 0.1 kPa to 100 MPa.

19. The process of claim 18, wherein the oxygenate feedstock is contacted with the molecular sieve catalyst at a pressure in the range of 6.9 kPa to 34 MPa.

20. The process of claim 19, wherein the oxygenate feedstock is contacted with the molecular sieve catalyst at a pressure in the range of 48 kPa to 0.34 Mpa.

21. The process of claim 14, wherein the oxygenate feedstock is mixed with a diluent comprising at least one compound selected from the group consisting of helium, argon nitrogen, carbon monoxide, carbon dioxide, hydrogen, water, paraffins, and aromatic compounds.

22. A process for converting an oxygenate feedstock into an olefin product stream comprising:
   mixing together a regenerated molecular sieve catalyst and a molecular sieve catalyst having less than 1.0 wt % carbonaceous deposits comprising carbonaceous deposits thereon, wherein the mix comprises 2–30 2 wt % carbonaceous deposits based on the total weight of the mix; and
   contacting the catalyst mix with oxygenate feedstock under conditions effective to convert the feedstock into an olefin product stream comprising $C_2$–$C_3$ olefins.

23. The process of claim 22, wherein the mix comprises 2–20 wt % carbonaceous deposits.

24. The process of claim 22, wherein the regenerated molecular sieve catalyst comprises 0.5 wt % or less carbonaceous deposits.

25. The process of claim 22, wherein the oxygenate feedstock is contacted with the catalyst mix in a riser reactor.

26. The process of claim 22, wherein the catalyst mix comprises catalyst having a pore diameter of less than 5.0 Angstroms.

27. The process of claim 26, wherein the catalyst is at least one catalyst selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted groups thereof.

28. The process of claim 26, wherein the catalyst is at least one catalyst selected from the group consisting of ZSM-5, ZSM-4, erionite, and chabazite.

29. The process of claim 26, wherein the catalyst is at least one catalyst selected from the group consisting of SAPO-34, SAPO-17, and SAPO-18.

30. The process of claim 26, wherein the catalyst is a MeAPSO.

31. The process of claim 22, wherein the catalyst mix comprises catalyst having a pore diameter of 5–10 Angstroms.

32. The process of claim 31, wherein the catalyst is at least one catalyst selected from the group consisting of MFI, MEL, MTW, EUO, MTT, HEU, FER, AFO, AEL, TON, and substituted groups thereof.

33. The process of claim 22, wherein the oxygenate feedstock comprises at least one compound selected from the group consisting of methanol, ethanol, n-propanol, isopropanol, C4–C10 alcohols, methyl ether, dimethyl ether, diethyl ether di-isopropyl ether, methyl mercaptan, methyl sulfide, methyl amine, ethyl mercaptan, di-ethyl sulfide, di-ethyl amine, ethyl chloride, formaldehyde, di-methyl carbonate, di-methyl ketone, acetic acid, n-alkyl amines, n-alkyl halides, and n-alkyl sulfides, wherein the n-alkyl groups comprise from 3–10 carbon atoms.

34. The process of claim 22, wherein the oxygenate feedstock is contacted with the catalyst mix at a temperature in the range of 200–700° C.

35. The process of claim 34, wherein the oxygenate feedstock is contacted with the catalyst mix at a temperature in the range of 250–600° C.

36. The process of claim 35, wherein the oxygenate feedstock is contacted with the catalyst mix at a temperature in the range of 300–500° C.

37. The process of claim 34, wherein the oxygenate feedstock is contacted with the catalyst mix at a pressure in the range of 0.1 kPa to 100 MPa.

38. The process of claim 37, wherein the oxygenate feedstock is contacted with the catalyst mix at a pressure in the range of 6.9 kPa to 0.34 MPa.

39. The process of claim 38, wherein the oxygenate feedstock is contacted with the catalyst mix at a pressure in the range of 48 kPa to 0.34 Mpa.

40. The process of claim 33, wherein the oxygenate feedstock is mixed with a diluent comprising at least one compound selected from the group consisting of helium, argon nitrogen, carbon monoxide, carbon dioxide, hydrogen, water, paraffins, and aromatic compounds.

41. The process of claim 14, wherein the oxygenate feedstock comprises methanol.

42. The process of claim 33, wherein the oxygenate feedstock comprises methanol.

* * * * *

UNITED STATES PATENT AND TRADEMARK OFFICE
CERTIFICATE OF CORRECTION

PATENT NO.    : 6,023,005                                        Page 1 of 1
DATED         : February 8, 2000
INVENTOR(S)   : James Richardson Lattner, Hsiang-ning Sun, Stephen Neil, Vaughn, Keith H. Kuechler, David C. Skouby It is certified that error appears in the above-identified patent and that said Letters Patent is hereby corrected as shown below:

Column 10,
Line 34, replace "2-30 2 wt%" with "2-30 wt%"

Signed and Sealed this

Twenty fifth Day of September, 2001

*Attest:*

*Attesting Officer*

NICHOLAS P. GODICI
*Acting Director of the United States Patent and Trademark Office*